US006255542B1

(12) United States Patent
Mais et al.

(10) Patent No.: US 6,255,542 B1
(45) Date of Patent: Jul. 3, 2001

(54) PROCESS FOR PREPARING 2-CHLORO-4-NITROALKYLBENZENE

(75) Inventors: Franz-Josef Mais, Düsseldorf; Helmut Lahr, Odenthal, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 21 days.

(21) Appl. No.: 09/643,114

(22) Filed: Aug. 21, 2000

(30) Foreign Application Priority Data

Aug. 27, 1999 (DE) ............................................. 199 40 861

(51) Int. Cl.$^7$ .................................................. C07C 205/12
(52) U.S. Cl. ............................................ 568/937; 568/940
(58) Field of Search ...................................... 568/937, 940

(56) References Cited

U.S. PATENT DOCUMENTS

| 3,005,031 | 10/1961 | Friedrich | 260/646 |
| 3,341,595 | 9/1967 | Doering | 260/580 |
| 3,920,757 | 11/1975 | Watson | 260/623 H |
| 4,456,777 | 6/1984 | Petruck et al. | 568/937 |
| 5,095,157 | 3/1992 | Mais et al. | 568/940 |

FOREIGN PATENT DOCUMENTS

| 193 662 | 2/1982 | (CS) . |
| 150587 | 8/1985 | (EP) . |
| 50-007589 | 3/1975 | (JP) . |
| 76842 | 8/1981 | (RO) . |

OTHER PUBLICATIONS

J. Chem. Soc. Oct. 1927, p. 2903, Scholfied, The Dimorphism of 2–Chloroaceto–p–toluidide.
Bull Soc. Chim. Belg., 61 pages 3316–317, (month unavailable) 1952, H. Vanderhaeghe et G. Derudder, Activité tuberculostatique des dérivés de l'acide 4. Amino–2–hydroxybenzoique (p.amino–salicylique).

Introduction to Organic Chemistry, 3$^{rd}$ edition, Andrew Streitwieser, Jr. and Clayton H. Heathcock pp. 669–670, Effects of Multiple Substituents 1990 (month unavailable).

Organic Chemistry, (month unavailable) 1985,John McMurry, pp. 506–507, Trisubstituted Benzenes: additivity of effects.

Methoden Der Organischen Chemie, (Houben–Weyl) vol. V/3 (month unavailable) 1962, p. 704 $\beta_6$) Austausch von Wasserstoff gegen Chlor in aromatischen Nitroverbindungen.

Naturwiss 17, (month unavailable) 1929, p. 13, Zuschriften.

Synthesis, (month unavailable) 1981, H.J. Christau et al et al, Synthesis of Diaryl Sulfide by Nickel(II)–Catalyzed Arylation of Arenethiolates, pp. 892–894.

J. Org. Chem., vol. 44, No. 2, (month unavailable) 1979, T.R. Forbus et al, pp. 313–314, Trifluoroacetyl Triflate: An Easily Accessible Highly Electrophilic Trifluoroacetylating Agent.

*Primary Examiner*—Samuel Barts
(74) *Attorney, Agent, or Firm*—Joseph C. Gil; Diderico van Eyl

(57) ABSTRACT

A process for preparing 2-chloro-4-nitroalkylbenzenes is provided which comprises a ring chlorination of 4-nitroalkylbenzenes with elemental chlorine or chlorine-releasing compounds in liquid phase and in the presence of Friedel-Crafts catalysts and specific sulphur-containing aromatic compounds as co-catalysts.

20 Claims, No Drawings

PROCESS FOR PREPARING 2-CHLORO-4-NITROALKYLBENZENE

FIELD OF THE INVENTION

The invention relates to a process for preparing 2-chloro-4-nitroalkylbenzenes by ring chlorination of 4-nitroalkylbenzenes with elemental chlorine or chlorine-releasing compounds in liquid phase and in the presence of Friedel-Crafts catalysts and sulphur-containing aromatic compounds as co-catalysts.

BACKGROUND OF THE INVENTION

The reaction of 4-nitrotoluene with chlorine in the presence of Lewis acid catalysts such as $FeCl_3$ (U.S. Pat. No. 3,341,595; J. Chem. Soc. 1927, 2905) or $SbCl_3$ (Bull. Soc. Chim. Belg. 61 (1952) 317) is known. The main product formed is the desired 2-chloro-4-nitrotoluene. This result can also be explained using the generally applicable substituent rules for electrophilic aromatic substitution. The textbooks Streitwieser, Jr. and Heathcock "Introduction to Organic Chemistry" 1985, 669–670 (MacMillan Publishing Co.) and McMurry "Organic Chemistry", 1985, 506–507 (Brooks-Cole Publishing Co.), for example, show that the effect of the methyl group and the para-nitro group is additive, and that the most preferred position for the entry of the third substituent is the ortho position to the methyl group. However, as by-products, there are also observed more highly chlorinated, positionally isomeric dichloro-4-nitrotoluenes and 4-nitrobenzyl chloride, and the ring-chlorinated derivatives derived therefrom.

However, it is not possible to gain any understanding of the stepwise selectivity in the electrophilic aromatic substitution from the general substitution rules mentioned. In the present case of the ring chlorination of 4-nitroalkylbenzenes, stepwise selectivity is understood as how big the proportion of the desired monochlorinated product is in the reaction mixture, based on the conversion of 4-nitroalkylbenzene. In general, such chlorinations proceed with high selectivity at the beginning of the reaction, when virtually pure starting material is present. Thus, in accordance with the substituent rules mentioned, 2-chloro-4-nitroalkylbenzene is formed almost exclusively. However, in the course of the chlorination, the 4-nitroalkylbenzene content of the reaction mixture is being reduced, and simultaneously its 3-chloro-4-nitroalkylbenzene content increases. This additionally results in the desired product being chlorinated as well, reacting to give useless dichloronitroalkylbenzenes.

Our own studies on the ring chlorination of 4-nitrotoluene using $FeCl_3$ as catalyst have shown that the stepwise selectivity is still insufficient. The maximum proportion of 2-chloro-4-nitrotoluene which can be achieved in the reaction mixture is just below 90%. This result correlates well with the data from RO 76842 (CA 100: 8516 (1984)). This publication states a 2-chloro4-nitrotoluene content of 86 to 89% for chlorination mixtures of 4-nitrotoluene.

Furthermore, it is known that the stepwise selectivity of the chlorination of 4-nitroalkylbenzenes can be increased by additional co-catalysts.

Small amounts of iodine, for example, can be used as co-catalyst (Naturwiss. 17 (1929) 13, Houben-Weyl "Methoden der organischen Chemie" [Methods of organic chemistry] Volume V/3 (1962), 704, JP-B-75/7589 (CA 83:113927 (1975), CS 193662 (1984)). In addition, U.S. Pat. No. 3,005,031 describes that moist 4-nitrotoluene can be chlorinated in the presence of iron, iodine and $PCl_3$. Our own studies on the effect of iodine on the stepwise selectivity have shown, that a content of up to 95% of 2-chloro-4-nitrotoluene can be achieved in the reaction mixture under these conditions.

However, the process with addition of iodine has considerable disadvantages, rendering it unsuitable for industrial application. In particular, virtually all of the iodine remains in the chlorination mixture, even after repeated washing with water, so that even after catalytic hydrogenation and distillation, a 3-chloro-4-alkylaniline which is contaminated with iodine is obtained. Such a contaminated material cannot, for example, be used for phosgenation to 3-chloro4-alkylphenyl isocyanate.

German Offenlegungsschrift 31 28 442, too, discloses the chlorination of 4-nitrotoluene using iodine as the only catalyst. The chlorination is carried out at a temperature between the melting point of 4-nitrotoluene and 120° C. 0.1 to 10% by weight of iodine, based on 4-nitrotoluene, are employed. This process likewise affords chlorination mixtures with a high content of iodine, which are unsuitable for use in practice. Moreover, in this process a large fraction of the chlorine that is introduced escapes from the reaction mixture without being utilized, so that, for example, to achieve an industrially required conversion of more than 90 mol % of chlorine, up to 300 mol % of chlorine have to be introduced per mole of 4-nitrotoluene.

EP-A-0 399 293, too, describes the ring monochlorination of 2-chloro4-nitroalkylbenzenes. The co-catalysts used here are heterocyclic 5- or 6-membered dibenzo-fused compounds which contain at least one sulphur atom. The dibenzo-fused sulphur heterocycles used are, for example, compounds from the classes of the phenoxathiins, the thianthrenes, the thianthrene 5-oxides, the thianthrene 5,5-dioxides or the dibenzothiophenes. By this route, it is possible to obtain good selectivities. Contents of, for example, 95 to 96% of 2-chloro4-nitrotoluene in the chlorination mixture are achieved. However, this process, too, has considerable disadvantages which do not permit use in large-scale industrial practice. For example, the co-catalysts have to be synthesized via relatively complicated processes, since they are not commercially available. Furthermore, there are considerable objections from a toxicological point of view against the compounds from the classes mentioned.

Accordingly, it was an object of the present invention to provide an industrially applicable process for the ring chlorination of 4-nitroalkylbenzenes which has an increased stepwise selectivity. This process should ensure, in particular at high degrees of chlorination, when the proportion of 4-nitroalkylbenzene in the reaction mixture is already very low, that the proportion of more highly chlorinated products formed is low. Such a desired increase in the stepwise selectivity is equivalent to an increase in the yield of the target product 2-chloro-4-nitroalkylbenzene.

SUMMARY OF THE INVENTION

The present invention provides a process for preparing 2-chloro-4-nitroalkylbenzenes of the formula I

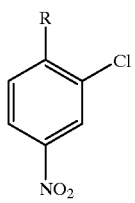

(I)

in which R represents a straight-chain or a branched $C_1$–$C_4$-alkyl group by ring chlorination of the parent 4-nitroalkylbenzene with elemental chlorine or chlorine-releasing compounds in liquid phase and in the presence of a Friedel-Crafts catalyst and a sulphur-containing co-catalyst, characterized in that the sulphur-containing aromatic co-catalysts used are diaryl sulphides of the formula II

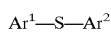   (II)

in which $Ar^1$ and $Ar^2$ independently of one another represent phenyl or naphthyl or phenyl which is mono- or polysubstituted by straight-chain or branched $C_1$–$C_8$-alkyl, straight-chain or branched $C_1$–$C_8$-halogenoalkyl, straight-chain or branched $C_1$–$C_8$-alkoxy, straight-chain or branched $C_1$–$C_8$-alkylmercapto, halogen, cyano, nitro, hydroxyl, phenylmercapto or phenyl groups. These and other features, aspects, and advantages of the present invention will become better understood with reference to the following description and appended claims.

DESCRIPTION OF THE INVENTION

The ring chlorination process according to the invention has excellent stepwise selectivity. Examples of the compounds which are, according to the invention, to be monochlorinated in the 2-position are 4-nitrotoluene, 4-nitroethylbenzene, 4-nitropropylbenzene and 4-nitro-n-butylbenzene. The process according to the invention is particularly suitable for the chlorination of 4-nitrotoluene.

Preference is given to using co-catalysts in which $Ar^1$ and $Ar^2$ are phenyl or phenyl which is mono- to trisubstituted by fluorine, chlorine or bromine atoms, straight-chain or branched $C_1$–$C_4$-alkyl groups, $C_1$–$C_4$-halogenoalkyl groups, $C_1$–$C_4$-alkylmercapto or phenyl groups. Particular preference is given to using co-catalysts in which $Ar^1$ and $Ar^2$ are phenyl or phenyl which is mono- or disubstituted by chlorine, bromine or methyl. The use of diphenyl sulphide, 4,4'-dibromodiphenyl sulphide, 4-chloro-4'-trifluoromethyldiphenyl sulphide, 4,4'-dicyanodiphenyl sulphide and 4,4'-dihydroxydiphenyl sulphide has been found to be particularly suitable. Furthermore, it is also possible to use mixtures of two or more co-catalysts according to the invention.

The diaryl sulphides of the formula II to be used according to the invention such as diphenyl sulphide, are either commercially available, or they can be prepared by numerous methods known per se. It is possible, for example, to react aryl halides with hydrogen sulphide or salts thereof or with aryl mercaptans or salts thereof (see, for example, H. J. Cristau et al., Synthesis 1981, 892), or to react sulphur halides or arylsulphonyl halides or cyanides with aromatic compounds (see, for example, T. R. Forbus et al., J. Org. Chem. 1979 (44), 313).

The process according to the invention is carried out in a liquid phase, and the 4-nitroalkylbenzene of the formula I is employed in liquid (molten) form or, if appropriate, diluted with an inert solvent. Suitable solvents are those which are inert to chlorine and/or the catalyst system under the conditions of the process according the invention. Such solvents are known, in principle, to the person skilled in the art and include, for example, methylene chloride, chloroform, carbon tetrachloride and acetic acid. The process is preferably carried out without solvent.

The preferred chlorinating agent for the process according to the invention is chlorine, which can be introduced in liquid or gaseous form into the reaction mixture; preference is given to introducing gaseous chlorine. However, it is also possible to use other chlorinating agents which release chlorine under the reaction conditions, e.g., sulphuryl chloride.

In principle, the process according to the invention can be carried out at a temperature from the melting point to the boiling point of the reaction mixture. In general, the reaction temperature is 50 to 1 50° C., preferably 70 to 120° C. and particularly preferably 80 to 100° C. The reaction pressure can be atmospheric, reduced or elevated and is, in principle, immaterial. Owing to the reaction apparatus being more simple, preference is given to carrying out the reaction at atmospheric pressure. It may be advantageous to increase the pressure if a low-boiling reaction mixture with a low-boiling solvent is to be kept in the liquid phase. In this case, preference is given to operating under the automatically resulting autogenous pressure of such a reaction mixture.

Using the process according to the invention, it is possible to selectively prepare a 2-chloro-4-nitroalkylbenzene, i.e., a monochlorinated compound. For such a monochlorination, 90 to 130 mol %, preferably 95 to 110 mol %, of chlorine in elemental form or in the form of a chlorine-releasing substance are employed per mole of 4-nitroalkylbenzene.

A low water content of the reaction mixture is generally not critical. All starting materials can therefore preferably be used in a form which is not dried specifically. However, it is, of course, also possible to dry some or all starting materials completely. A low water content is understood as a water content which does not exceed the saturation limits of the starting materials in question. Furthermore, such a low water content must not be so high that the Friedel-Crafts catalyst employed is completely consumed by hydrolysis. Low water contents in the reaction mixture of up to 250 ppm, preferably up to 150 ppm are, for example, possible.

Suitable Friedel-Crafts catalysts for the process according to the invention are all Friedel-Crafts catalysts known to the person skilled in the art such as antimony chlorides, aluminium chloride or iron chlorides. However, it is also possible to use elements or element compounds which form a Friedel-Crafts catalyst (Lewis acid) during the chlorination. These include elements such as iron, antimony, aluminium or zinc, as well as the oxides, sulphides or carbonyls of these elements. Further, salts of weak acids such as the carbonates can be used. It is possible to employ, for example, antimony oxides, iron oxides, iron sulphides, iron carbonyls or iron carbonates. Instead of the chlorides mentioned, it is also possible to use the bromides and, if appropriate, the fluorides of the elements mentioned. Preferred Friedel-Crafts catalysts are antimony chlorides and iron chlorides, and particular preference is given to iron(III) chloride.

The use quantities of the Friedel-Crafts catalyst or a mixture of a plurality of Friedel-Crafts catalysts can be varied within wide limits. Thus, a catalytic effect is noticeable even when 0.005% by weight is added. On the other hand, it is also possible to add 10% by weight or more of the Friedel-Crafts catalyst. However, such large amounts generally do not offer any advantage, but are cost-intensive and, if appropriate, lead to problems during work-up. The Friedel-Crafts catalyst or a mixture of a plurality of Friedel-Crafts catalysts is usually employed in an amount of 0.01 to 3% by weight, preferably 0.05 to 1.5% by weight, particularly preferably 0.1 to 1.00% by weight, in each case based on the amount of the 4-nitro-alkylbenzene employed.

The co-catalysts according to the invention or mixtures of a plurality of co-catalysts can be employed in amounts which can vary within wide limits. However, the co-catalytic effect is reduced in the case of amounts below 0.01% by weight. Quantities of more than 10% by weight do not offer any further advantage, but again, they are cost-intensive and can cause problems during work-up. In general, the co-catalysts according to the invention are thus employed in amounts of 0.01 to 5% by weight, preferably 0.05 to 2.5% by weight, particularly preferably 0.1 to 1% by weight, in each case based on the 4-nitroalkylbenzene employed.

In the process according to the invention, the molar ratio of the co-catalysts to the Friedel-Crafts catalysts employed can likewise be varied within wide limits. In general, it is advantageous to employ the co-catalyst in amounts which are neither too much of an excess nor too substoichiometric with respect to the Friedel-Crafts catalyst. Therefore, in general, a molar ratio of Friedel-Crafts catalyst to co-catalyst of from about 50:1 to about 1:10, preferably from about 10:1 to about 1:5, particularly preferably from about 3:1 to about 1:2.5 is chosen.

When the process according to the invention is carried out in practice, the individual components of the reaction mixture can be added in any order. The process can be carried out both continuously and batchwise. The following paragraph describes an exemplary embodiment.

The desired 4-nitroalkylbenzene, e.g., 4-nitrotoluene, is initially charged and heated to, for example, 90° C. The desired amounts of Friedel-Crafts catalyst(s) and co-catalyst (s) are then added in any order, and whilst the temperature is essentially kept constant, gaseous chlorine in the predetermined amount is introduced. The mixture is subsequently worked up in a customary manner, for example, by distillation.

The following is a further exemplary embodiment: a solution of catalyst and co-catalyst in the desired 4-nitro-alkylbenzene is prepared and heated to the desired reaction temperature. A chlorinating agent is then added in the intended amount. Here, too, work-up can be carried out by distillation.

The process according to the invention is characterized by an extremely high selectivity for the desired monochlorinated product. It permits chlorination mixtures with a 2-chloro-4-nitrotoluene content of up to 95 to 96% to be obtained. This is surprising, in particular, with respect to U.S. Pat. No. 5,095,157, which describes, as co-catalysts, only very particular complex sulphur-containing heterocycles.

However, the diaryl sulphides according to the invention are surprisingly just as effective and, on the other hand, much more easily accessible. The process according to the invention completely avoids the disadvantages of iodine-containing chlorination mixtures.

The invention is further described in the following illustrative examples in which all parts and percentages are by weight unless otherwise indicated.

EXAMPLES

In the examples below, the following abbreviations were used:

NT: 4-nitrotoluene
2-CNT: 2-chloro-4-nitrotoluene
3-CNT: 3-chloro-4-nitrotoluene
DiCNT: sum of the three possible dichloro-4-nitrotoluenes
Remainder: sum of all other components The selectivity for the formation of the 2-chloro4-nitroalkylbenzene was defined as follows:

$$\text{Selectivity } S = \frac{\text{content of 2-CNT} \times 100}{100 - \text{residual content of 4-NT}}$$

Comparative Example 1 (no co-catalyst)

In a darkened slim chlorination beaker, 315 g of 4-nitrotoluene and 1.89 g of anhydrous $FeCl_3$ were initially charged and, at 90° C., 231 g of chlorine were introduced at a uniform rate with stirring, over a period of 7.5 hours. At predetermined intervals, samples were taken from the reaction mixture and examined by gas chromatography. The results were summarized in the table below:

| $Cl_2{}^{1)}$ mol % | NT % | 2-CNT % | 3-CNT % | DiCNT % | Remainder % | Selectivity 2-CNT |
|---|---|---|---|---|---|---|
| 39.8 | 63.89 | 35.07 | 0.34 | 0.27 | 0.52 | 97.12 |
| 76.6 | 32.33 | 65.28 | 0.50 | 1.50 | 0.41 | 96.47 |
| 89.4 | 21.72 | 74.98 | 0.50 | 2.38 | 0.42 | 95.78 |
| 108.4 | 9.02 | 85.70 | 0.42 | 4.38 | 0.38 | 94.19 |
| 119.4 | 2.48 | 89.05 | 0.27 | 7.70 | 0.50 | 91.31 |
| 130.4 | 0.19 | 85.17 | 0.09 | 13.82 | 0.73 | 85.33 |
| 141.6 | 0.02 | 76.91 | 0.01 | 21.89 | 1.17 | 76.92 |

$^{1)}$amount of chlorine metered in in mol %, based on the amount of 4-nitrotoluene employed Comparative Example 2 (iodine as co-catalyst)

In a darkened chlorination beaker, 315 g of 4-nitrotoluene, 1.89 g of anhydrous $FeCl_3$ and 94.5 mg of iodine were initially charged, and the mixture was heated at 70° C. With stirring, 186 g of chlorine were introduced over the course of 7 hours. At predetermined intervals, samples were taken and analysed by GC. The results are summarized in the table below:

| $Cl_2{}^{1)}$ mol % | NT | 2-CNT | 3-CNT | DiCNT | Remainder | Selectivity 2-CNT |
|---|---|---|---|---|---|---|
| 39.8 | 64.46 | 34.83 | 0.16 | 0.11 | 0.42 | 99.00 |
| 77.2 | 31.10 | 67.64 | 0.23 | 0.73 | 0.30 | 98.17 |
| 90.6 | 18.70 | 79.58 | 0.21 | 1.22 | 0.29 | 97.88 |
| 108.4 | 4.50 | 92.41 | 0.12 | 2.67 | 0.30 | 96.76 |
| 114.5 | 1.28 | 94.85 | 0.06 | 3.50 | 0.30 | 96.07 |

$^{1)}$amount of chlorine metered in in mol %, based on the amount of 4-nitrotoluene employed After the introduction of chlorine, the mixture was flushed with $N_2$ for 30 min and then washed 3x with in each case 125 g of water at about 70° C. This gave 393.3 g of an organic product phase which was slightly moist and had a 2-chloro-4-nitrotoluene content of 94.85 GC area per cent. This product was analyzed for iodine. It had a total iodine content of 220 ppm.

The meanings of the abbreviations in the table are identical to Comparative Example 1.

Example 3

(Diphenyl sulphide as co-catalyst)

In a darkened chlorination beaker, 407 g of 4-nitrotoluene, 3.1 g of anhydrous $FeCl_3$ and 3.1 g of diphenyl sulphide were initially charged and, at 90° C. and with stirring, 242 g of gaseous chlorine were introduced at a uniform rate over the course of 3.75 hours. At predetermined intervals, samples were taken from the reaction mixture and examined by GC. The results are summarized in the table below:

| $Cl_2^{1)}$ mol % | NT | 2-CNT | 3-CNT | DiCNT | Remainder | Selectivity 2-CNT |
|---|---|---|---|---|---|---|
| 55.8 | 47.24 | 52.02 | 0.07 | 0.17 | 0.50 | 98.60 |
| 71.2 | 31.94 | 66.94 | 0.08 | 0.32 | 0.72 | 98.35 |
| 103.1 | 4.79 | 93.22 | 0.05 | 1.41 | 0.53 | 97.91 |
| 104.4 | 1.51 | 95.66 | 0.03 | 2.17 | 0.73 | 97.03 |
| 111.0 | 0.07 | 94.30 | 0.01 | 4.83 | 0.79 | 94.37 |
| 114.9 | 0.03 | 92.16 | 0.01 | 6.87 | 0.93 | 92.19 |

1)amount of chlorine metered in in mol %, based on the amount of 4-nitrotoluene employed Example 4

(4,4'-dibromodiphenyl sulphide as co-catalyst)

In a darkened chlorination beaker, 291 g of 4-nitrotoluene, 2.2 g of anhydrous $FeCl_3$ and 4.1 g of 4,4'-dibromodiphenyl sulphide were initially charged and heated with stirring to 90° C., and 196 g of gaseous chlorine were introduced at this temperature at a uniform rate over the course of 4 hours. At predetermined intervals, samples are taken and analysed by GC. The results are summarized in the table below:

| $Cl_2^{1)}$ mol % | NT | 2-CNT | 3-CNT | DiCNT | Remainder | Selectivity 2-CNT |
|---|---|---|---|---|---|---|
| 98.2 | 16.07 | 82.02 | 0.09 | 0.85 | 0.91 | 97.80 |
| 104.8 | 10.84 | 87.03 | 0.08 | 1.12 | 0.93 | 97.61 |
| 110.8 | 7.09 | 90.43 | 0.07 | 1.45 | 0.96 | 97.33 |
| 114.8 | 5.24 | 91.99 | 0.66 | 1.83 | 0.88 | 97.08 |
| 120.1 | 2.15 | 94.28 | 0.04 | 2.55 | 0.98 | 96.35 |
| 124.7 | 1.02 | 94.59 | 0.03 | 3.33 | 1.03 | 95.56 |
| 130.0 | 0.60 | 93.79 | 0.02 | 4.33 | 1.06 | 94.36 |

1)amount of chlorine metered in in mol %, based on the amount of 4-nitrotoluene employed After the introduction of chlorine ended, the mixture was, at 90° C., flushed with nitrogen for 1 hour. After cooling, a yield of 360.4 g was obtained. Taking into account a loss of 4 g for the samples taken during the course of the reaction, this corresponds, at a final content of 93.79% of 2-chloro4-nitrotoluene, to a calculated yield of 94.0% of theory.

Example 5

(4-chloro-4'-trifluoromethyidiphenyl sulphide as co-catalyst)

The process of Example 3 was repeated, but using, instead of the co-catalyst employed therein, 4.75 g of 4-chloro4'-trifluoromethyidiphenyl sulphide, and introducing 253 g of chlorine over 3.5 hours. The result is summarized in the table below:

| $Cl_2^{1)}$ mol % | NT | 2-CNT | 3-CNT | DiCNT | Remainder | Selectivity 2-CNT |
|---|---|---|---|---|---|---|
| 90.2 | 15.44 | 85.29 | 0.08 | 0.80 | 1.09 | 97.67 |
| 100.1 | 7.01 | 90.36 | 0.07 | 1.48 | 1.08 | 97.17 |
| 104.9 | 3.48 | 93.15 | 0.05 | 2.22 | 1.10 | 96.51 |
| 110.1 | 0.84 | 94.09 | 0.03 | 3.75 | 1.29 | 94.89 |
| 114.8 | 0.14 | 92.02 | 0.01 | 6.65 | 1.18 | 92.15 |
| 120.1 | 0.06 | 87.68 | 0.01 | 10.89 | 1.36 | 87.73 |

1)amount of chlorine metered in in mol %, based on the amount of 4-nitrotoluene employed Example 6

(4,4'-dicyanodiphenyl sulphide as co-catalyst)

The process of Example 3 was repeated, but using, instead of the co-catalyst employed therein, 5.20 g of 4,4'-dicyanodiphenyl sulphide and, instead of 3.1 9, 4.1 g of anhydrous $FeCl_3$. At 90° C., 275 g of chlorine were introduced over 4.5 hours. The result is summarized in the table below:

| $Cl_2^{1)}$ mol % | NT | 2-CNT | 3-CNT | DiCNT | Remainder | Selectivity 2-CNT |
|---|---|---|---|---|---|---|
| 100.6 | 20.06 | 77.74 | 0.09 | 0.71 | 1.40 | 97.25 |
| 110.6 | 13.41 | 84.08 | 0.08 | 0.95 | 1.48 | 97.10 |
| 120.0 | 7.76 | 89.40 | 0.07 | 1.24 | 1.52 | 96.92 |
| 125.3 | 5.11 | 91.83 | 0.06 | 1.51 | 1.49 | 96.78 |
| 130.5 | 2.80 | 93.97 | 0.05 | 1.86 | 1.50 | 96.49 |

1)amount of chlorine metered in in mol %, based on the amount of 4-nitrotoluene employed.

After flushing, a yield of 503.5 g was obtained. Taking into account the samples of about 3 g and the content of 93.79%, the resulting yield was 93.3% of theory of 2-chloro-4-nitrotoluene.

Example 7

(4,4'-dihydroxydiphenyl sulphide as co-catalyst)

The process of Example 3 was repeated, but using, instead of the co-catalyst employed therein, 3.6 g of 4,4'-dihydroxydiphenyl sulphide. At 90° C., 295 g of chlorine were introduced over 4.5 hours. The result was summarized in the table below:

| $Cl_2^{1)}$ mol % | NT | 2-CNT | 3-CNT | DiCNT | Remainder | Selectivity 2-CNT |
|---|---|---|---|---|---|---|
| 100.1 | 23.34 | 73.96 | 0.26 | 1.93 | 0.51 | 96.48 |
| 110.6 | 16.07 | 80.57 | 0.25 | 2.56 | 0.55 | 96.00 |
| 120.5 | 9.79 | 85.92 | 0.23 | 3.46 | 0.60 | 95.24 |
| 130.0 | 5.32 | 89.18 | 0.20 | 4.63 | 0.67 | 94.19 |
| 140.0 | 1.93 | 90.44 | 0.14 | 6.74 | 0.57 | 92.22 |

1)amount of chlorine metered in in mol %, based on the amount of 4-nitrotoluene employed.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing 2-chloro4-nitroalkylbenzenes of the formula I:

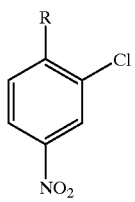   (I)

in which R represents a straight-chain or a branched $C_1$–$C_4$-alkyl group;

said process comprising ring chlorinating 4-nitroalkylbenzene with elemental chlorine or chlorine-releasing compounds in a liquid phase and in the presence of a Friedel-Crafts catalyst and a sulphur-containing aromatic co-catalyst, wherein the aromatic co-catalyst is a diaryl sulphide of the formula $$Ar^1—S—Ar^2$$

in which each $Ar^1$ and $Ar^2$ is a phenyl group or a naphthyl group, or a phenyl group that is mono- or polysubstituted by (i) a straight-chain or a branched $C_1$–$C_8$-alkyl group, (ii) a straight-chain or a branched $C_1$–$C_8$-halogenoalkyl group, (iii) a straight-chain or a branched $C_1$–$C_8$-alkoxy group, (iv) a straight-chain or a branched $C_1$–$C_8$-alkylmercapto group, (v) a halogen, (vi) a cyano group, (vii) a nitro group, (viii) a hydroxyl group, (ix) a phenylmercapto group or (x) a phenyl group.

2. The process of claim 1, wherein the compound of the formula I is selected from the group consisting of 4-nitrotoluene, 4-nitroethylbenzene, 4-nitropropylbenzene and 4-nitro-n-butylbenzene.

3. The process of claim 1, wherein each $Ar^1$ and Ar2 group of the co-catalyst represents (i) a phenyl group or (ii) a phenyl group that is mono- to trisubstituted by a member selected from the group consisting of fluorine, chlorine or bromine, straight-chain $C_1$–$C_4$-alkyl groups, branched $C_1$–$C_4$-alkyl groups, $C_1$–$C_4$-halogenoalkyl groups, $C_1$–$C_4$-alkylmercapto groups and phenyl groups.

4. The process of claim 1, wherein each $Ar^1$ and $Ar^2$ group of the co-catalysts represents a member selected from the group consisting of phenyl groups and phenyl groups that are mono- or disubstituted by chlorine, bromine or methyl groups.

5. The process of claim 1, wherein the process is carried out at a reaction temperature ranging from about 50 to about 150° C.

6. The process of claim 1, wherein the process is carried out at a reaction temperature ranging from about 70 to about 120° C.

7. The process of claim 1, wherein the process is carried out at a reaction temperature ranging from about 80 to about 100° C.

8. The process of claim 1, wherein from about 90 to about 130 mol % of chlorine in elemental form or in the form of a chlorine-releasing substance are employed per mole of 4-nitroalkylbenzene.

9. The process of claim 1, wherein from about 95 to about 110 mol % of chlorine in elemental form or in the form of a chlorine-releasing substance are employed per mole of 4-nitroalkylbenzene.

10. The process of claim 1, wherein the Friedel-Crafts catalysts are selected from the antimony chlorides, aluminium chloride or iron chlorides.

11. The process of claim 10, wherein the iron chloride Friedel-Crafts catalysts are iron(Ill) chlorides.

12. The process of claim 1, wherein the Friedel-Crafts catalyst or a mixture of a plurality of Friedel-Crafts catalysts is employed in an amount ranging from about 0.01 to about 3% by weight, based on the amount of the 4-nitro-alkylbenzene employed.

13. The process of claim 1, wherein the mixture of a plurality of Friedel-Crafts catalysts is employed in an amount ranging from about 0.05 to about 1.5% by weight, based on the amount of the 4-nitroalkylbenzene employed.

14. The process of claim 1, wherein the mixture of a plurality of Friedel-Crafts catalysts is employed in an amount of ranging from about 0.1 to about 1.00% by weight, based on the amount of the 4-nitroalkyl-benzene employed.

15. Process according to claim 1, wherein the co-catalyst or a mixture of a plurality of co-catalysts is employed in an amount ranging from about 0.01 to about 5% by weight, based on the amount of the 4-nitro-alkylbenzene employed.

16. The process of claim 1, wherein the co-catalyst or a mixture of a plurality of co-catalysts is employed in an amount ranging from about 0.05 to about 2.5% by weight, based on the amount of the 4-nitroalkylbenzene employed.

17. The process of claim 1, wherein the co-catalyst or a mixture of a plurality of co-catalysts is employed in an amount ranging from about 0.1 to about 1% by weight, based on the amount of the 4-nitroalkylbenzene employed.

18. The process according to claim 1, wherein the molar ratio of Friedel-Crafts catalyst to co-catalyst ranges from about 50:1 to about 1:10.

19. The process of claim 1, wherein the molar ratio of Friedel-Crafts catalyst to co-catalyst is from about 10:1 to about 1:5.

20. The process of claim 1, wherein the molar ratio of Friedel-Crafts catalyst to co-catalyst is from about 3:1 to about 1:2.5.

* * * * *